United States Patent [19]

MacAlpine et al.

[11] Patent Number: 4,822,937

[45] Date of Patent: Apr. 18, 1989

[54] PROCESS FOR THE PRODUCTION OF ISOBUTYLBENZENES

[75] Inventors: Derek K. MacAlpine; Malcolm J. Lawrenson, both of North Humberside, England

[73] Assignee: BP Chemicals Limited, London, England

[21] Appl. No.: 198,685

[22] Filed: May 24, 1988

Related U.S. Application Data

[63] Continuation of Ser. No. 89,021, Aug. 24, 1987, abandoned, which is a continuation of Ser. No. 913,649, Sep. 15, 1985, abandoned.

[30] Foreign Application Priority Data

Feb. 23, 1985 [GB] United Kingdom ............... 8504707

[51] Int. Cl.$^4$ ..................... C07C 1/00; C07C 5/32
[52] U.S. Cl. ..................... 585/319; 585/364; 585/431; 585/435
[58] Field of Search ............... 585/319, 364, 431, 435

[56] References Cited

U.S. PATENT DOCUMENTS

| | | | |
|---|---|---|---|
| 4,010,217 | 3/1977 | Zuech | 585/364 |
| 4,367,358 | 1/1983 | Wideman et al. | 585/430 |
| 4,375,571 | 3/1983 | Hart et al. | 585/431 |
| 4,429,175 | 1/1984 | Cihonski | 585/434 |

*Primary Examiner*—Curtis R. Davis
*Attorney, Agent, or Firm*—Nixon & Vanderhye

[57] ABSTRACT

A process for the production of isobutylbenzenes in particular, isobutylbenzene itself, is provided. The process is in two stages and comprises (1) reacting a vinylcyclohexane with an isoolefin of formula $(R)(R^1)C=C(CH_3)_2$ in the presence of a dismutation catalyst to produce an isobutenylcyclohexene and (2) contacting the isobutenylcyclohexene with a dehydroisomerisation catalyst to produce an isobutylbenzene. Examples of vinylcyclohexenes which can be used include 4-vinylcyclohexene and styrene.

13 Claims, No Drawings

PROCESS FOR THE PRODUCTION OF ISOBUTYLBENZENES

This application is a continuation of Ser. No. 089,021, filed Aug. 24, 1987, now abandoned, which is a Rule 62 continuation of U.S. Ser. No. 913,649, filed Sept. 15, 1986, now abandoned.

The present invention relates to a process for the production of isobutylbenzene from a vinylcyclohexene. In particular the invention relates to a two stage process for producing isobutylbenzene from a vinylcyclohexene having as its first stage a dismutation reaction.

Isobutylbenzene is a high value speciality chemical used, for example, as an intermediate in the preparation of analgesics. Conventionally, isobutylbenzene is produced industrially by the side chain alkylation of toluene with propylene using an alkali metal catalyst. The alkali metal catalyst can be a liquid potassium, a liquid potassium/sodium eutectic or an alkali metal supported on a diatomaceous earth as disclosed in for example U.S. Pat. No. 3,449,455. The above process has a number of disadvantages when operated commercially since the alkali metal catalyst is (a) expensive, (b) inflammable and difficult to handle and (c) short lived owing to gum formation. In addition there is formed, as a byproduct, substantial quantities of n-butylbenzene which has to be separated subsequently from the isobutylbenzene.

A two stage process has now been devised which avoids the problems associated with the alkylation route and allows isobutylbenzene to be produced selectively. An important feature of this process as described herein is that a vinylcyclohexene is used as a feedstock, in place of toluene and that in the first stage of the process the vinylcyclohexene undergoes dismutation with an isoolefin to produce an isobutenylcyclohexene, for example,

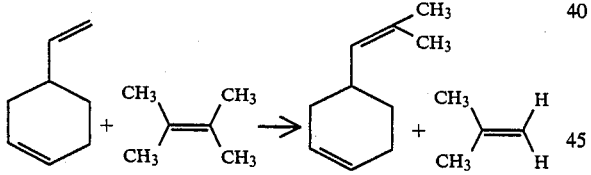

which can subsequently be converted to isobutylbenzene in the second stage.

Accordingly, the present invention provides a process for the production of an isobutylbenzene from a vinylcyclohexene and an isoolefin which process comprises (1) in a first stage contacting the vinylcyclohexene and isoolefin with a dismutation catalyst under dismutation conditions to produce an isobutenylcyclohexene and another olefin, (2) in a second stage contacting the isobutenylcyclohexene produced in the first stage with a dehydroisomerisation catalyst at elevated temperature to produce the isobutylbenzene.

The first stage of the process described above is a dismutation reaction between a vinylcyclohexene and an isoolefin. If the vinylcyclohexene used is a vinylcyclohexa-mono-ene then it is preferable to use 4-vinylcyclohexene as this is the most readily available. The cyclohexene ring of the vinylcyclohexene can be substituted with alkyl or aryl groups in which case substituted isobutenylcyclohexenes and ultimately substituted isobutylbenzenes are produced. A homodismutation product of the vinylcyclohexene can be used in place of the vinylcyclohexene itself when the isoolefin 2,3-dimethylbut-2-ene is used because in this case only a single product is produced in the dismutation reaction. For example when 1,2-dicyclohex-4-enylethene is used the reaction proceeds according to the equation:

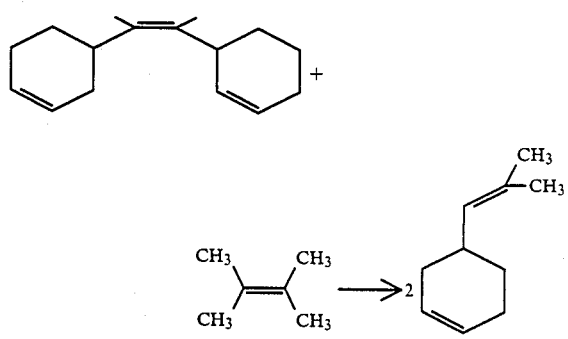

It is a feature of the first stage of the process described above that although the vinylcyclohexene possesses two double bonds (one cyclic in the cyclohexene ring and one exocyclic outside the ring) it is only the exocyclic double bond which undergoes dismutation. This preference of the dismutation catalyst for exocyclic double bonds means that the reaction can be carried out using any vinylcyclohexene, i.e. a vinylcyclohexa-mono-ene, a vinylcyclohexa-di-ene or a vinylcyclohexa-triene vinylcyclohexa-triene (i.e. a styrene or a stilbene).

As regards the isoolefin, this has a formula

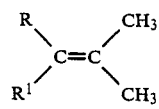

where R and $R^1$ are independently hydrogen or hydrocarbyl radicals. The hydrocarbyl radicals are suitably $C_1$ to $C_6$ alkyl groups. Preferred isoolefins are isobutene ($R=R^1=H$), 2,3-dimethylbut-2-ene ($R=R^1=CH_3$), and 2-methylbut-2-ene ($R=H$; $R^1=CH_3$), 2-methylpent-2-ene ($R=H$, $R^1=C_2H_5$) and 2,4,4-trimethylpent-2-ene ($R=H$, $R^2=C_4H_9$).

The first stage of the process described above is catalysed by a dismutation catalyst. The dismutation catalyst is suitably a tungsten, molybdenum or rhenium containing catalyst. Preferably the dismutation catalyst is rhenium heptoxide supported on alumina (UK No. 1,054,846) or alumina phosphated by a method described in our UK Pat. No. 1,414,488. Catalysts of this type may be prepared, for example, by impregnating the alumina or phosphated alumina with ammonium perrhenate and subsequently heating the impregnated material in air to convert the perrhenate to the oxide.

The rhenium containing catalysts in the form described above can be used to catalyse the dismutation reaction between the vinylcyclohexene and all the isoolefins disclosed above with the exception of isobutene. When isobutene is used as co-feed with the vinylcyclohexene little reaction occurs with catalysts comprising only rhenium heptoxide and alumina or phosphated alumina. The isobutene/vinycyclohexene dismutation reaction may be promoted, however, by addition of an organometallic derivative of tin, lead, aluminium or germanium. Preferred promoters are organometallic derivatives of tin e.g. tetramethyl tin $(CH_3)_4Sn$, tetraphenyl tin $(C_6H_5)_4Sn$ and the like. Promoted catalysts can also be used with the other isoolefins to improve reaction rates.

The promoter can be impregnated on to the catalyst at levels of up to 20% by weight or it can be introduced into the reactor at a low level with the vinylcyclohexene and isoolefin feedstocks.

As regards the reaction conditions under which the first stage is operated, it is preferable to work at a temperature in the range 0° to 90° C. and at a pressure in the range atmospheric pressure to 50 bar. The contact time of the feedstocks on the catalyst preferably lie in the range 5 mins to 60 mins.

The product of the first stage of the process consists of an isobutenylcyclohexene, together with another olefin. The other olefin will be that which is the other dismutation product of the reaction and will depend on the particular feedstock isoolefin used in the first stage. For example, if the feedstock isoolefin is isobutene the other olefin produced will be ethylene.

The product of the first stage can either be fed directly to the second stage of the process or indirectly via a separation stage, where the isobutenylcyclohexene is separated from the other olefin prior to being fed to the second stage.

The first stage of the process may be carried out either batchwise or continuously.

In the second stage of the process, the direct or indirect product of the first stage is dehydroisomerised to an isobutylbenzene. The dehydroisomerisation reaction is effected by contacting the direct or indirect first stage product at temperatures of ambient or above with a dehydroisomerisation catalyst. Suitable dehydroisomerisation catalysts include supported alkali metals e.g. potassium on alumina, or supported Group VIII metals, such as Pd, Pt, Rh, Os or Ir, on an alumina. The dehydroisomerisation catalyst can be prepared by any conventional technique familiar to the skilled man. The loading of alkali metal or Group VIII metal on the support should be in the range 0.01 to 20% by weight.

As regards temperature of reaction this should be ambient or above.

The invention is illustrated by reference to the following examples.

EXAMPLES OF STAGE 1

Example 1

51 g of 8-15 BSS mesh gamma-alumina, obtained from calcining a commercially available boehmite alumina (CATAPAL SB from Vista) at 580° C., was impregnated with a 40 ml aqueous solution of 3.6 g ammonium perrhenate, evaporated to dryness, dried in vacuo at 110° C. for 6 hours, and activated for 24 hours at 580° C. in a stream of air. The catalyst so prepared was found to contain 5.5% by weight $Re_2O_7$.

A "U" tube steel reactor was charged with 60 ml of the catalyst. This operation was carried out in a glove box under a nitrogen atmosphere. The charged reactor was then installed, under a rigorous nitrogen blanket, on to a unit consisting of a feed tank, a pump, a drier charged with 200 ml of 3A molecular sieve, a treater charged with 200 ml of 2% sodium on potassium carbonate, a reactor sited in a heated fluidised alumina bath, a water cooled condenser, and a product tank. A homogeneous feed, consisting of 4-vinylcyclohexene and isobutene in the molar ratio 1:3, was pumped at 120 ml/h (LHSV=2) over the catalyst bed at 30° C. with an operating pressure of 23.3 bar. The products were collected and analysed at regular intervals by standard gas chromatographic methods. The reaction conditions and results are given in Table 1.

Example 2

The process of Example 1 was repeated except that the catalyst was prepared from a commerically available gamma-alumina (ACTAL I from Laporte). The reaction conditions and results are given in Table 1.

Example 3

The process of Example 1 was repeated except that the reactor was heated to 70° C. The reaction conditions and results are given in Table 1.

Example 4

The process of Example 1 was repeated except that the catalyst was prepared from a commercially available gamma-alumina as 1 mm spheres (UM 708 CB from Universal Matthey Products). The reaction conditions and results are given in Table 1.

Example 5

The process of Example 1 was repeated except that the catalyst was prepared from 35 g of a commercially available gamma-alumina as 1 mm spheres (UM 708 CB from Universal Matthey Products) and impregnated with a 50 ml aqueous solution of 5 g ammonium perrhenate. The catalyst so prepared was found to contain 10.7% by weight $Re_2O_7$. The reaction conditions and results are given in Table 1.

Example 6

The process of Example 1 was repeated except that the catalyst was impregnated with tetramethyltin before use. The catalyst so prepared contained 18.5% by weight $SnMe_4$. The reaction conditions and results are given in Table 1.

Example 7

The process of Example 6 was repeated except that the feed consisted of 4-vinylcyclohexene and isobutene in the molar ratio of 1:10. The catalyst contained 16.4% $SnMe_4$. The reaction conditions and results are given in Table 1.

Example 8

The process of Example 7 was repeated except that the reactor was heated to 57° C. The catalyst contained 18.0% $SnMe_4$. The reaction conditions and results are given in Table 1.

Example 9

The process of Example 7 was repeated with a catalyst containing 5.0% $SnMe_4$. The reaction conditions and results are given in Table 1.

Example 10

The process of Example 9 was repeated except that the LHSV was increased to 4. The reaction conditions and results are given in Table 1.

Example 11

The process of Example 9 was repeated except that the LHSV was increased to 10. The reaction conditions and results are given in Table 1.

Example 12

The process of Example 7 was repeated with a catalyst containing 3.0% SnMe₄. The reaction conditions and results are given in Table 1.

Example 13

The process of Example 7 was repeated with a catalyst containing 1.0% SnMe₄. The reaction conditions and resuts are given in Table 1.

g of feed and the reactor was sealed. The feed consisted of 4-vinylcyclohexene and 2-methyl-2-pentene in the molar ratio of 1:4. After 120 minutes, at ambient temperature, the products were analysed by standard gas chromatographic methods. The results indicated that 82.2% of the 4-vinylcyclohexene was converted affording dismutation products with the following selectivities 3.8% cis-4-n-butenylcyclohexene 33.0% 4-isobutenylcyclohexene, 58.8% trans-4-n-butenylcyclohexene, and 4.4% 1,2-dicyclohex-4-enylethene.

Example 15

3.1 g of the catalyst prepared in Example 14 was charged into the reactor. 10.3 g of a feed, consisting of 4-vinylcyclohexene and 2-methyl-2-butene in the molar

TABLE 1

| Example No. | 1 | 2 | 3 | 4 | 5 | 6 | 7 |
|---|---|---|---|---|---|---|---|
| Alumina base | CATAPAL SB | ACTAL I | CATAPAL SB | UM 708 CB | UM 708 CB | CATAPAL SB | CATAPAL SB |
| Re₂O₇ loading | 5.5 | 6 | 6 | 6.4 | 10.7 | 6 | 6 |
| % Wt of SnMe₄ | Nil | Nil | Nil | Nil | Nil | 18.5 | 16.4 |
| Food ratio 4VCH:Isobutene | 1:3 | 1:3 | 1:3 | 1:3 | 1:3 | 1:3 | 1:10 |
| LHSV | 2 | 2 | 2 | 2 | 2 | 2 | 2 |
| Reactor temperature, °C. | 30 | 30 | 70 | 30 | 30 | 30 | 30 |
| % 4VCH converted | 6.8 | 3.2 | 10.8 | 2.9 | 3.8 | 19.1 | 25.0 |
| % Weight IBCH Selectivity DCHE of products | 51.0 49.0 | 42.4 57.6 | 56.9 43.1 | 50.7 49.3 | 30.1 69.9 | 57.7 42.3 | 72.5 27.5 |
| % yield of isobutene dimer | 1.0 | 42.0 | 7.4 | 11.9 | 62.7 | 0.02 | 0.01 |
| Half life, hours | 24 | 24 | 24 | 24 | 24 | 10 | 12 |

| Example No. | 8 | 9 | 10 | 11 | 12 | 13 |
|---|---|---|---|---|---|---|
| Alumina base | CATAPAL SB | CATAPAL SB | CATAPAL SB | CATAPAL SB | CATAPAL SB | CATAPAL SB |
| Re₂O₇ loading | 6 | 6 | 6 | 6 | 6 | 6 |
| % Wt of SnMe₄ | 18.0 | 5.0 | 5.0 | 5.0 | 3.0 | 1 |
| Food ratio 4VCH:Isobutene | 1:10 | 1:10 | 1:10 | 1:10 | 1:10 | 1:10 |
| LHSV | 2 | 2 | 4 | 10 | 2 | 2 |
| Reactor temperature, °C. | 57 | 30 | 30 | 30 | 30 | 30 |
| % 4VCH converted | 33.8 | 35.8 | 34.4 | 29.5 | 35.5 | 38.0 |
| % Weight IBCH Selectivity DCHE of products | 77.5 22.5 | 75.2 24.8 | 74.8 25.2 | 78.2 21.8 | 74.4 25.6 | 74.4 25.6 |
| % yield of isobutene dimer | 0.6 | 0.1 | 0.04 | 0.04 | 0.1 | 0.2 |
| Half life, hours | 10 | 12 | 3 | 1½ | 9 | 5 |

VCH = 4-vinylcyclohexene
IBCH = 4-isobutenylcyclohexene
DCHE = 1,2-dicyclohex-4-enylethene

Example 14

70 g of a commercially available gamma-alumina (PURALOX SG from Condea) was digested for 6 hours at 80° C. in 250 ml of an aqueous solution containing 5 g of ammonium phosphate dibasic [(NH₄)₂HPO₄]. Distilled water was added as necessary to keep the alumina covered. The resultant slurry was filtered and washed with 2 liters of distilled water. This material was dried at 110° C. overnight and then calcined at 580° C. for 16 hours in a current of air.

38 g of the phosphated alumina was subsequently impregnated with a 50 ml aqueous solution of 1.30 g ammonium perrhenate, evaporated to dryness, dried in vacuo at 120° C. for 6 hours, and activated for 24 hours at 580° C. in a stream of dry air. The catalyst so prepared was kept at ambient temperature under an inert atmosphere.

5.9 g of the catalyst was charged into a glass reactor under a blanket cover of nitrogen. To this was added 17 ratio of 1:4, was added and the reactor sealed. After 90 minutes, at ambient temperature, the products were analysed and the results were as follows; 91.2% of the 4-vinylcyclohexene was converted affording dismutation products with the following selectivities 2.2% iso-4-propenylcyclohexene, 75.0% trans-4-propenyl cyclohexene, 17.3% 4-isobutenylcyclohexene and 5.7% 1,2-dicyclohex-4-enylethene.

Example 16

58 g 1/16″ extrudate gamma-alumina, obtained from calcining the commerically available boehmite alumina (PURAL NG from Condea) at 580° C., was impregnated with a 80 ml aqueous solution of 8.64 g ammonium perrhenate, evaporated to dryness, dried in vacuo at 110° C. for 6 hours at 580° C. in a stream of dry air. The catalyst so prepared was found to contain 10.4% by weight Re₂O₇.

14.5 g of the catalyst was charged into the reactor with 29 g of a feed consisting of styrene and 2-methyl-2-pentene in the molar ratio of 1:25. The reactor was sealed, and after 90 minutes, at ambient temperature, the products were analysed. The results were as follows; 69.9% of the styrene was converted affording dismutation products with the following selectivities 7.5% cis-n-butenylbenzene, 3.3% isobutenylbenzene, 80.3% trans-n-butenylbenzene, 0.9% cis-stilbene, and 7.9% trans-stilbene.

Example 17

35 g of a commercially available gamma-alumina as 1 mm spheres (UM 708 CB from Universal Matthey Products) was impregnated with a 50 ml aqueous solution of 5 g ammonium perrhenate, evaporated to dryness, dried in vacuo at 110° C. for 6 hours, and activated for 24 hours at 580° C. in a stream of air. The catalyst so prepared was found to contain 10.7% by weight $Re_2O_7$.

6 g of the catalyst was charged into the reactor with 22.8 g of a feed consisting of 4-vinylcyclohexene and 2,4,4-trimethyl-2-pentene in the moalr ratio of 1:2. The reactor was sealed, and after 90 minutes, at ambient temperature, the products were analysed. The results were as follows, 27% of the 4-vinylcyclohexene was converted affording dismutation products with the following selectivity 16.1% 4-isobutenylcyclohexene, 5.4% 2-cyclohex-4-enyl-3,3-dimethylbut-1-ene, 78.4% 1,2-dicyclohex-4-enylethene.

Example 18

51 g of 8-15 BSS mech gamma-alumina, obtained from calcining a commercially available boehmite alumina (CATAPAL SB from Vista) at 580° C., was impregnated with a 40 ml aqueous solution of 3.6 g ammonium perrhenate, evaporated to dryness, dried in vacuo at 110° C. for 6 hours, and activated for 24 hours at 580° C. in a stream of air. The catalyst so prepared was found to contain 5.5% by weight $Re_2O_7$.

4.4 g of the catalyst was charged into the reactor with 4.6 g of a feed consisting of 4-vinylcyclohexene and 2,3-dimethyl-2-butene in the molar ratio of 1:3. The reactor was sealed, and after 60 minutes, at ambient temperature, the products were analysed. The results were as follows, 81.7% of the 4-vinylcyclohexene was converted affording dismutation products with the following selectivity 78.9% of 4-isobutenylcyclohexene and 21.1% 1,2-dicyclohene-4-enylethene.

Example 19

The reaction apparatus comprised a feed tank, a pump, a feed treater containing 2% by weight sodium on potassium carbonate tablets, a cylindrical vertical reactor fitted with a water cooled jacket and centrally situated thermocouple and a product tank. Prior to use the apparatus was flushed with nitrogen.

The reactor was charged with 5 ml of catalyst. The catalyst used was prepared in the following way: 30 g of 8-15 mesh gamma-alumina obtained from calcining Condea SB boehmite alumina at 580° C. was impregnated with a 30 ml aqueous solution of 2.1 g of ammonium perrhenate, evaporated to dryness, dried in vacuo at 110° C. for 6 hours and activated for 24 hours at 580° C. in a stream of dry air. The catalyst so prepared was found to contain 6.2% by weight $Re_2O_7$.

The feed tank was charged with dry 4-vinylcyclohexene (49.5% purity; 71 ml) and dry 2-methylpentene-2 (98.5% purity; 200 ml). The feed was pumped at 30 ml/hour over the catalyst bed at 14° C., with an operating pressure of 1.2 barg.

Analysis of the collected products for the period 4 hours to 5 hours showed a 4-VCH conversion of 86.4%, a ratio of IBCH/NBCH=0.65 and a ratio of hexene 3/IBCH=0.82.

Example 20

The reaction apparatus was as previously. The catalyst was prepared as in Example 1.

The reactor was charged with 11.3 mls of catalyst. The feed tank was charged with dry 4-vinylcyclohexene and dry 2,4,4-trimethylpentene-2 in a molar ratio of 1:10. The feed was pumped at 20-25 ml/hour over the catalyst bed, initially at 17° C., after 19 hours the temperature was raised to 50° C.

Analysis of the collected products for the period 1-2 hours to 15-16 hours and 19-20 hours are shown in Table 2.

Example 21

The reaction apparatus used was as previously. The catalyst was prepared as in Example 1 and then impregnated with 5% w/w tetramethyltin.

The reactor was charged with 20 ml of the tetramethyltin impregnated catalyst. The feed tank was charged with dry 4-vinylcyclohexene (35 ml) and dry 2,4,4-trimethylpentene-2 (420 ml). The feed was pumped over the catalyst bed at a rate of 40 ml/hour at 50° C. at an operating pressure of 0.4 barg.

Analysis of collected products for the periods 1-2 hours and 4-5 hours are shown in Table 2.

TABLE 2

| Example | Temperature | Sample Time | 4-VCH Conversion | 4-VCH Selectivity to IBCH | 4-VCH Selectivity to DCHE | 4-VCH Selectivity to NHCH | % by weight isomerisation of 2,4,4-trimethyl pentene-2 to 2,4,4-trimethyl pentene-1 |
|---|---|---|---|---|---|---|---|
| 20 | 17° C. | 1-2 hours | 86.0% | 58.1% | 20.0% | 4.2% | 23.5% |
|  | 17° C. | 15-16 hours | 76.0% | 57.0% | 20.9% | 3.5% | 9.4% |
|  | 50° C. | 19-20 hours | 87.0% | 57.3% | 19.4% | 8.2% | 40.0% |
| 21 | 50° C. | 1-2 hours | 99.2% | 68.2% | 0.7% | 31.1% | 2.5% |
|  | 50° C. | 4-5 hours | 98.2% | 64.3% | 16.6% | 19.1% | 2.0% |

Example 22

The process of Example 18 was repeated except that the catalyst was impregnated with tetramethyltin before use and the feed was 27 g of isobutene and 9.6 g of 1,2-dicyclohex-4-enylethene. The catalyst so prepared contained 6.4% by weight $SnMe_4$. After 30 minutes reaction the products were analysed. 13.7% of the 1,2-dicyclohex-4-enylethylene was converted affording dismutation products with the following seectivities 54% 4-isobutenylcyclohexene and 4.6% 4-vinylcylohexene.

Example 23

13.1 g of the cataysts prepared in Example 17 was charged into a steel reactor under a blanket of nitrogen. To this was added 8.4 g of 1,2-dicyclohex-4-enyl ethylene and 27 g of isobutene. The reactor was sealed and rocked. After 1 hour at ambient temperature, the products were analysed. 3.7% of the 1,2-dicyclohex-4-vinyl ethylene was converted affording dismutation products with the following selectivities 31.3% 4-isobutenylcyclohexene and 69.% 4-vinylcyclohexene.

EXAMPLE OF SECOND STAGE

Example 24

A palladium on alumina catalyst (0.5% wt Pd) was packed into a quartz tube in a vertically mounted furnace equipped with a temperature controller. The catalyst was heated from room temperature to 550° C. under a stream of nitrogen (10 liters/hour) and maintained at this temperature for 12 hours. The catalyst was then cooled to 350° C. The nitrogen flow was reduced to 0.98 liters/hour, and degassed 4-isobutenylcyclohexene passed over the catalyst in vapour form. After contact with the catalyst, the vapour/nitrogen mixture was cooled and any condensable products trapped by means of a water condenser. Analysis of the condensed product obtained after 1 hour (using GLC techniques) showed a 100% conversion of 4-isobutenylcyclohexene with a 95% seectivity to isobutylbenzene.

We claim:

1. A process for the production of an isobutylbenzene from a vinylcyclohexene selected from the group consisting of a vinylcyclohexa-mono-ene, a vinylcyclohexa-di-ene and a vinylcyclohexa-triene and an isoolefin having the formula:

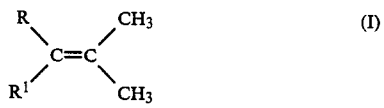

wherein R and R$^1$ are independently either hydrogen or C$_1$ to C$_6$ alkyl groups, which process comprises:
 (1) in a first stage contacting the vinylcyclohexene and the isoolefin with a dismutation catalyst under dismutation conditions to produce an isobutenylcyclohexene, and
 (2) in a second stage contacting the isobutenylcyclohexene produced in the first stage with a dehydroisomerisation catalyst at elevated temperature to produce an isobutylbenzene.

2. A process according to claim 1, wherein the vinylcyclohexa-mono-ene is 4-vinylcyclohexene.

3. A process according to claim 1, wherein the vinylcyclohexa-mono-ene is 1,2-dicylcohexa-4-enylethene.

4. A process according to claim 1, wherein the isoolefin is selected from isobutene, 2,3-dimethylbut-2-ene, 2-methylbut-2-ene, 2-methylpent-2-ene and 2,4,4-trimethylpent-2-ene.

5. A process according to claim 1, wherein the isoolefin is 2,3-dimethylbut-2-ene.

6. A process according to claim 1, wherein the dismutation catalyst used in the first stage is rhenium heptoxide supported on either alumina or phosphated alumina.

7. A process according to claim 1, wherein the dismutation catalyst is promoted with an organometallic derivative of either tin, lead, aluminum or germanium.

8. A process according to claim 7, wherein the organometallic derivative is either tetramethyl tin or tetraphenyl tin.

9. A process according to claim 1, wherein the isoolefin is a compound of the formula (I) wherein R and R$^1$ are different and the products of the first stage comprising an isobutenylcyclohexene and another olefin are separated in an intermediate stage into an isobutenylcyclohexene fraction and a fraction comprising the other olefin and wherein the isobutenylcyclohexene fraction is fed to the second stage.

10. A process according to claim 1, wherein the dehydroisomerisation catalyst used in the second stage is potassium supported on alumina.

11. A process according to claim 1, wherein the dehydroisomerisation catalyst used in the second stage is either palladium, platinum, rhodium, osmium or indium supported an alumina.

12. A process according to claim 1, wherein said vinylcyclohexa-mono-ene is selected from the group consisting of 4-vinylcyclohexene, 1,2-dicyclohexa-4-enylethene and cyclohexene ring-substituted alkyl or aryl derivatives thereof.

13. A process according to claim 1, wherein said vinylcyclohexa-triene is selected from the group consisting of a styrene and a stilbene.

* * * * *